US012644114B2

(12) United States Patent
Yang et al.

(10) Patent No.: US 12,644,114 B2
(45) Date of Patent: Jun. 2, 2026

(54) IN VITRO RAPID SYNTHESIS OF MEDIUM- AND HIGH-COPY DNA REPEATS BASED ON BLOCKING POLYMERASE CHAIN REACTION

(71) Applicant: Tsinghua University, Beijing (CN)

(72) Inventors: Xuerui Yang, Beijing (CN); Xin Wang, Beijing (CN)

(73) Assignee: Tsinghua University, Beijing (CN)

( * ) Notice: Subject to any disclaimer, the term of this patent is extended or adjusted under 35 U.S.C. 154(b) by 849 days.

(21) Appl. No.: 17/757,140

(22) PCT Filed: Dec. 11, 2019

(86) PCT No.: PCT/CN2019/124559
§ 371 (c)(1),
(2) Date: Jun. 9, 2022

(87) PCT Pub. No.: WO2021/114135
PCT Pub. Date: Jun. 17, 2021

(65) Prior Publication Data
US 2023/0027474 A1　Jan. 26, 2023

(51) Int. Cl.
| | |
|---|---|
| *C07H 21/02* | (2006.01) |
| *C12N 15/10* | (2006.01) |
| *C12P 19/34* | (2006.01) |

(52) U.S. Cl.
CPC .......... *C12N 15/1031* (2013.01); *C12P 19/34* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

FOREIGN PATENT DOCUMENTS

| | | |
|---|---|---|
| CN | 1278558 A | 1/2001 |
| CN | 102154269 A | 5/2012 |
| CN | 102031250 A | 6/2012 |
| CN | 110229871 A | 9/2019 |
| WO | WO 2004/009814 A1 | 1/2004 |
| WO | WO 2004/061119 A2 | 7/2004 |
| WO | WO 2017/219929 A1 | 12/2017 |
| WO | WO 2019/162699 A1 | 8/2019 |

OTHER PUBLICATIONS

Sui et al., "Tandem blocking of PCR extension to form a single-stranded overhang for facile, visual, and ultrasensitive gene detection" RSC Adv., 2018,8, 15652-15658.
Written opinion of International Searching Authority issued in PCT/CN2019/124559 issued Jun. 17, 2021.

*Primary Examiner* — Frank W Lu
(74) *Attorney, Agent, or Firm* — KNOBBE, MARTENS, OLSON & BEAR, LLP

(57) ABSTRACT

The invention provides a method for synthesizing a DNA sequence comprising repeat units, including designing and synthesizing an extension primer and a blocking primer based on the repeat unit, performing a PCR amplification reaction by using the repeat unit (as an amplification template), the extension primer, and the blocking primer in a PCR reaction system, to obtain the DNA sequence comprising repeat units. The invention also provides a kit for this method. The method of the invention has the characteristics such as controllable copy number for repeat synthesis, simple synthesis steps, and low cost, and is very suitable for high-throughput production in industry.

9 Claims, 7 Drawing Sheets

Specification includes a Sequence Listing.

Linear template　Template cyclization

T4 ligase　Exo I　Exo III

Ligation　Digestion of single-strand molecule

Cyclized template

RCA
(Cyclized amplification)

Linear template

Template cyclization

T4 ligase

Ligation

Exo I

Exo III

Digestion of single-strand molecule

Cyclized template

RCA
(Cyclized amplification)

Once PCR

Gene of interest a

Once PCR

Twice PCR

Thrice PCR

Four-time PCR

Gene of interest b

A

B

A

Sustained-release profile of doxorubicin

B

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial sequence
<220> FEATURE:
<223> OTHER INFORMATION: RU sequence

<400> SEQUENCE: 1
ggagagctgt ggacttcgtc                                                    20

<210> SEQ ID NO 2
<211> LENGTH: 26
<212> TYPE: DNA
<213> ORGANISM: Artificial sequence
<220> FEATURE:
<223> OTHER INFORMATION: TP sequence

<400> SEQUENCE: 2
gacgaagtcc acagctctcc gacgaa                                             26

<210> SEQ ID NO 3
<211> LENGTH: 14
<212> TYPE: DNA
<213> ORGANISM: Artificial sequence
<220> FEATURE:
<223> OTHER INFORMATION: BP sequence

<400> SEQUENCE: 3
gtccacagct ctcc                                                          14
```

IN VITRO RAPID SYNTHESIS OF MEDIUM- AND HIGH-COPY DNA REPEATS BASED ON BLOCKING POLYMERASE CHAIN REACTION

TECHNICAL FIELD

The invention relates to the technical field of DNA amplification, and in particular to a method for synthesizing a DNA sequence comprising repeat units. The invention also provides a kit for use in this method.

REFERENCE TO ELECTRONIC SEQUENCE LISTING

The present application is filed along with an Electronic Sequence Listing. The Electronic Sequence Listing is provided as a file entitled 55755730_1.txt which is approximately 1 kilobyte in size, created on Jun. 8, 2022. The information in the Electronic Sequence Listing is incorporated herein by reference in its entirety.

BACKGROUND

In recent years, with the improvement of sequencing capabilities, the genome information of many species has been deciphered, and a large number of DNA repeats have been discovered in succession. Moreover, the content of DNA repeats is positively correlated with the evolution of species. The types and contents of DNA repeats in eukaryotic genomes are much more than those in prokaryotes, thus indicating that repetitive DNA elements are directly related to biological evolution and complex biological functions, and have quite strong biological function and research significance. With the extension of genomics research, it has been found that DNA double-stranded sequences containing different copy numbers have significant differences in annealing kinetics. The repeat unit content and copy number are negatively correlated with the annealing time. Thus, according to the kinetic characteristics, DNA repeats are divided into: single-copy repetitive sequence; lowly repetitive sequence; moderately repetitive sequence; and highly repetitive sequence. Moderately and highly repetitive sequence elements are directly related to biological functions such as chromosome construction, structural maintenance, and regulation of gene expression. In addition, due to the self-assembly ability with strong affinity for moderately and highly repetitive DNA molecules, moderately and highly repetitive double-stranded DNA molecules per se are often the excellent basic molecules for the construction of biocompatible materials.

Given the above, the artificial synthesis of moderately and highly repetitive DNA sequences in vitro has quite important application values in physiological and material applications. The existing methods for synthesizing moderately and highly repetitive DNAs in vitro are relatively limited, mainly using RCA (rolling circle amplification) and gene synthesis and splicing techniques.

RCA mainly depends upon the cyclization amplification principle of viruses and prokaryotic plasmids, wherein the ligase is used for the cyclization ligation of certain single-stranded DNA molecules to obtain cyclized DNA template molecules, then a single-stranded DNA primer paired with the cyclized template and an efficient single-strand amplification enzyme (phi29) are used for the cyclic replication of cyclized template in an isothermal environment (25-37 degrees Celsius) to obtain single-stranded DNA repeats complementary to the cyclized template (as shown in FIG. 1). This method requires three steps: single-stranded template cyclization; uncyclized single-stranded DNA elimination; and cyclization amplification. It involves cumbersome operation steps, and the cost of biologically active enzymes required for each technical procedure is relatively higher, and thus the industrialization of this method is seriously limited. Additionally, the final product is a single-stranded repetitive DNA molecule. The later improved method MCH needs to additionally add more single-stranded primers to obtain a DNA double-stranded molecule product. The copy number of repetitive DNA molecules obtained by RCA method is positively correlated with the reaction time, that is, the copy number of the final product can only be controlled by controlling the reaction time. In practical operations, the length of the product is unpredictable, and it is difficult to precisely control the copy number of the repeats in the product, and thus it lacks practicability. Thus, the synthesis of moderately and highly repetitive DNAs using RCA amplification method has been stopped at the laboratory application stage, and it is difficult to use it in industry.

With the maturity of high-throughput DNA primer synthesis technique, the overlapping region amplification gene splicing method has gradually become the mainstream of gene synthesis (Gene SOE). In Gene SOE, long DNA fragments are divided into multi-stage small fragments, and each fragment has specific recognition base sequences on both sides, and the sequential assembly of multi-stage small fragments is completed with the assistance of ligase or amplification enzyme through the base complementarity principle, to finally obtain long DNA gene sequences (as shown in FIG. 2). The base length and base ratio in the overlapping region, as well as the Tm value of primer have a crucial impact on the overall splicing efficiency. However, when the copy number of highly repetitive DNA sequences reaches a certain threshold, base pairing slippage and mismatch will occur inside the DNA molecule. The amplification and ligation efficiencies will be seriously affected, resulting in problems such as decreased splicing efficiency and increased error rate, thereby resulting in longer period for synthesizing moderately and highly repetitive DNAs using the splicing method, high base mutation rate, uncontrollable copy number, and the like, and ultimately affecting the synthesis of repetitive DNA double-strands.

REFERENCE TO ELECTRONIC SEQUENCE LISTING

The present application is filed along with an Electronic Sequence Listing. The Electronic Sequence Listing is provided as a file entitled 55755730_1.txt which is approximately 1 kilobyte in size, created on Jun. 8, 2022. The information in the Electronic Sequence Listing is incorporated herein by reference in its entirety.

SUMMARY

In order to solve the problems such as high cost, long cycle length, and relatively higher error rate in the synthesis of repetitive sequence, the inventors have developed a novel method for rapidly synthesizing moderately and highly repetitive sequences in vitro.

The method of the invention involves the blocking PCR based repeat expansion (BPRE)). Based on a common chain polymerase amplification reaction, three complementarily paired DNA primer sequences are used. During the cyclic heating denaturation, the blocking primer template and the repeat unit template achieve steric hindrance pairing, exposing several (e.g., 6) bases at 3' end of the repeat unit template. The exposed several free base groups are paired with the complementary bases at the 3' end of the amplification primer (extension primer) template to form the primer-dimer, and complete the bidirectional amplification of the dimer under the action of the amplification enzyme (Taq DNA polymerase), so as to accomplish the accumulative extension of a repeat (as shown in the FIG. 3). The repetitive DNA double-stranded sequence newly generated is subjected to heating denaturation and cooling renaturation again, repeating the above-mentioned process of steric hindrance and dimer generation and extension, to finally accomplish the cumulative increase of highly repetitive DNA sequences. Thus, the cumulation of repeats in this method is positively correlated to the number of heating and cooling cycles.

Thus, the invention provides the following:

1. A method for synthesizing a DNA sequence comprising repeat units, comprising the following steps:

1) designing and synthesizing an extension primer and a blocking primer based on the repeat unit, wherein the difference between the blocking primer and the complementary sequence of the repeat unit lies in lacking n nucleotides at the 5' end of the complementary sequence (5' to 3' direction), and the difference between the extension primer and the complementary sequence of the repeat unit lies in adding the n nucleotides at the 3' end (5' to 3' direction), such that the extension primer and the blocking primer, when tandemly connected in the 5' to 3' direction, are exactly two complementary sequences for the repeat unit, wherein n is an integer from 3 to 20, preferably an integer from 4 to 10 (e.g., 4, 5, 6, 7, 8, 9, and 10); and 2) by using the repeat unit (as an amplification template), the extension primer (as an extension template for the repeat unit) and the blocking primer in a PCR reaction system, a PCR amplification reaction is performed, to obtain the DNA comprising repeat units. In the PCR reaction system, the blocking primer is first paired with the repeat unit (since the difference between the blocking primer and the complementary sequence of the repeat unit lies in lacking the n nucleotides at the 5' end of the complementary sequence (5' to 3' direction), the n nucleotides at the 3' end of the repeat unit are in an unpaired state), then the n nucleotides at the 3' end of the extension primer are paired with unpaired nucleotides in the repeat unit, and a PCR extension and amplification reaction is subsequently performed.

"DNA sequence comprising repeat units" in the invention is also referred to as a repetitive sequence (repeat). Repetitive sequences are widely present in the genome. According to the arrangement manner of repeat units, it can be divided into two categories: tandem repeats and interspersed repeats. Tandem repeats are repetitive sequences in which repeat units are tandemly connected end to end. The method of the invention is particularly suitable for the synthesis of tandem repeats. The length of the repeat unit (RU) is not particularly limited; for example, it may be 3~100 (e.g., 20, 30, 40, 50, 60, 70, 80, 90, or 100) nucleotides, preferably 10~30 nucleotides (e.g., 20, 21, 22, 23, 24, 25, 26, 27, 28, 29, or 30 nucleotides).

2. The method according to Item 1, further comprising a step of determining the copy number of the repeat units in the obtained DNA sequence, preferably by analyzing the molecular weight of PCR product via gel electrophoresis, or by DNA sequencing. The copy number of the repeat units in the DNA sequence obtained by the invention may range from 2 copies to thousands of copies, for example 5-200 copies, such as 10, 20, 30, 40, 50, 60, 70, 80, 90, and 100 copies.

3. The method according to Item 1, wherein the PCR reaction system further comprises PEG molecules, preferably having a molecular weight of 2,000~20,000 Da, and more preferably 4,000 Da, 6,000 Da, or 8,000 Da, and more preferably having a concentration in the PCR reaction system of 4 wt % to 20 wt % (e.g., 4 wt %, 8 wt %, and 12 wt %).

4. The method according to Item 3, wherein the PCR reaction system further comprises NaCl. In a preferred embodiment of the invention, when a new batch of primers is used, the effect of adding different concentrations of NaCl on the reaction product is tested, and an optimal concentration is selected. Preferably, the concentration of NaCl used in the PCR reaction system is 20~80 mM, preferably 30~60 mM.

5. The method according to Item 1, wherein the molar ratio of the repeat unit, the extension primer, and the blocking primer in the PCR reaction system is 1:1-10: 1-40, preferably 1:1:10.

6. The method according to Item 1, wherein the PCR amplification reaction is two-step PCR or three-step PCR.

By the PCR reaction system of the invention, the PCR reaction can be performed via any suitable PCR method known in the art.

Standard three-step PCR typically includes the following steps:

1) DNA denaturation: (90° C.-96° C.): hydrogen bonds in the double-stranded DNA template are cleaved under the action of heat to form a single-stranded DNA;

2) Annealing: (60° C.-65° C.): the system temperature is decreased such that the primer is combined with the DNA template to form a partially double-stranded molecule;

3) Extension: (70° C.-75° C.): under the action of Taq enzyme (with the best activity at around 72° C.), using dNTPs as raw materials, the extension is initiated from the 3' end of the primer in a direction of 5'→3' end, to synthesize a DNA strand complementary to the template.

For the copy number of PCR products, the fluorescein (ethidium bromide, EB)-stained gel electrophoresis is the most commonly used detection method. The electrophoretic detection is also a useful detection method. The fluorescent probe detection method is also useful.

The invention preferably adopts the two-step PCR, and its differences from the standard three-step PCR mainly lie in that:

1) the procedures are different: the annealing and extension are carried out at the same time in the two-step method to omit one heating and cooling process, while they are completed in two steps in the three-step method;

2) the consumed time is different: since one heating and cooling process is omitted in the two-step method, the reaction rate is improved and the consumed time is shorter.

7. The method according to any of Items 1 to 6, wherein the DNA sequence comprising repeat units is a lowly repetitive sequence, a moderately repetitive sequence or a highly repetitive sequence, preferably a moderately repetitive sequence or a highly repetitive sequence.

8. A kit for synthesizing a DNA sequence comprising repeat units, comprising a PCR reaction system comprising the repeat unit as an amplification template, an extension primer and a blocking primer, wherein the difference between the blocking primer and the complementary sequence of the repeat unit lies in lacking n nucleotides at the 5' end of the complementary sequence (5' to 3' direction), and the difference between the extension primer and the complementary sequence of the repeat unit lies in adding the n nucleotides at the 3' end (5' to 3' direction), such that the extension primer and the blocking primer, when tandemly connected in the 5' to 3' direction, are exactly two complementary sequences for the repeat unit, wherein n is an integer from 3 to 20, preferably an integer from 4 to 10 (e.g., 4, 5, 6, 7, 8, 9, and 10).

9. The kit according to Item 8, wherein:
1) the PCR reaction system further comprises PEG molecules, preferably having a molecular weight of 2,000~20,000 Da, and more preferably 4,000 Da, 6,000 Da, or 8,000 Da, and more preferably having a concentration in the PCR reaction system of 4 wt % to 20 wt % (e.g., 4 wt %, 8 wt %, and 12 wt %);
2) the PCR reaction system further comprises NaCl. When a new batch of primers is used, the effect of adding different concentrations of NaCl on the reaction product is tested, the optimal concentration is selected. Preferably, the concentration of NaCl used in the PCR reaction system is 20~80 mM, preferably 30~60 mM.
3) the molar ratio of the repeat unit, the extension primer, and the blocking primer in the PCR reaction system is 1:1-10:1-40, preferably 1:1:10; and/or
4) the PCR reaction system further comprises Taq DNA polymerase.

10. The kit according to Item 8 or 9, wherein the DNA sequence comprising repeat units is a lowly repetitive sequence, a moderately repetitive sequence or a highly repetitive sequence, preferably a moderately repetitive sequence or a highly repetitive sequence.

The method of the invention can indirectly control the copy number of repeats by controlling the number of heating and cooling cycles, and possesses the characteristics such as controllable copy number for repeat synthesis and simple synthesis steps, and is very suitable for industrialized high-throughput production. In addition, the present synthesis method only requires a single substance with biologically enzymatic activity and small amounts of three initial single-stranded DNA primers, has a microscale reaction system, and has no requirements for the primer purity (the reaction efficiency can be adjusted and calibrated by NaCl concentration during the synthesis process). It is far superior to the existing methods for the repeat synthesis in terms of economic benefits, greatly reducing the production cost and having significant cost advantages over the existing methods.

DESCRIPTION OF THE DRAWINGS

The above-mentioned features and advantages of the invention will become more apparent from the detailed descriptions below in conjunction with the accompanying drawings, wherein.

DESCRIPTION OF EMBODIMENTS

Unless otherwise indicated, the terms used herein have ordinary technical meanings as understood by those skilled in the art.

The invention is further illustrated in Examples below. These Examples are for illustrative purposes only and are not intended to limit the scope of the invention. The chemicals used in the reactions below are all commercially available products, unless otherwise indicated.

Example 1 Primer Design

Figure 1:
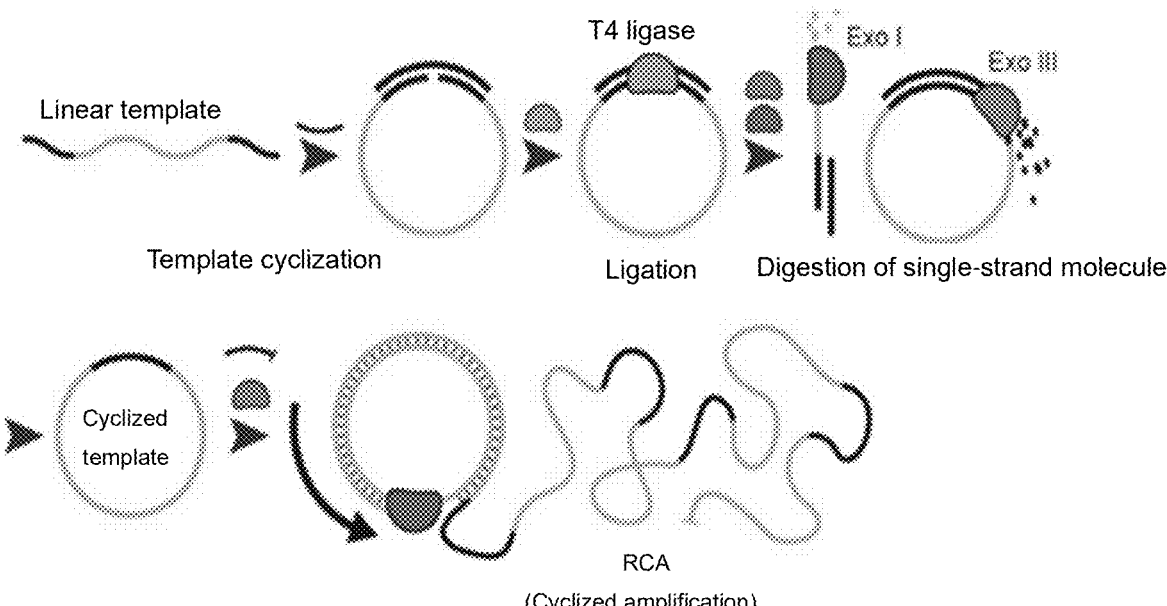
FIG. 1 is a schematic diagram of RCA (Rolling circle amplification) in the prior art.
Figure 2:
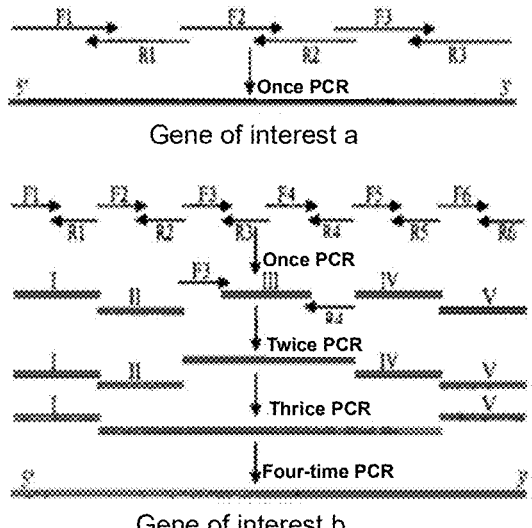
FIG. 2 is a schematic diagram of Gene SOE in the prior art.
Figure 3:
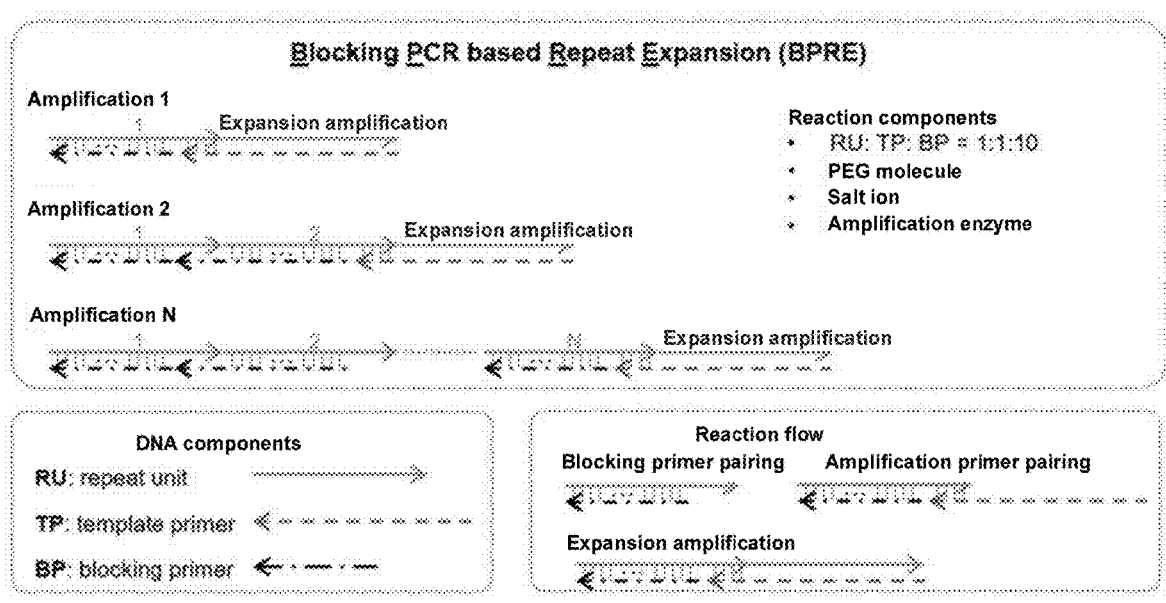
FIG. 3 is a schematic diagram of the blocking PCR based repeat expansion (BPRE) of the invention.
Figure 4:
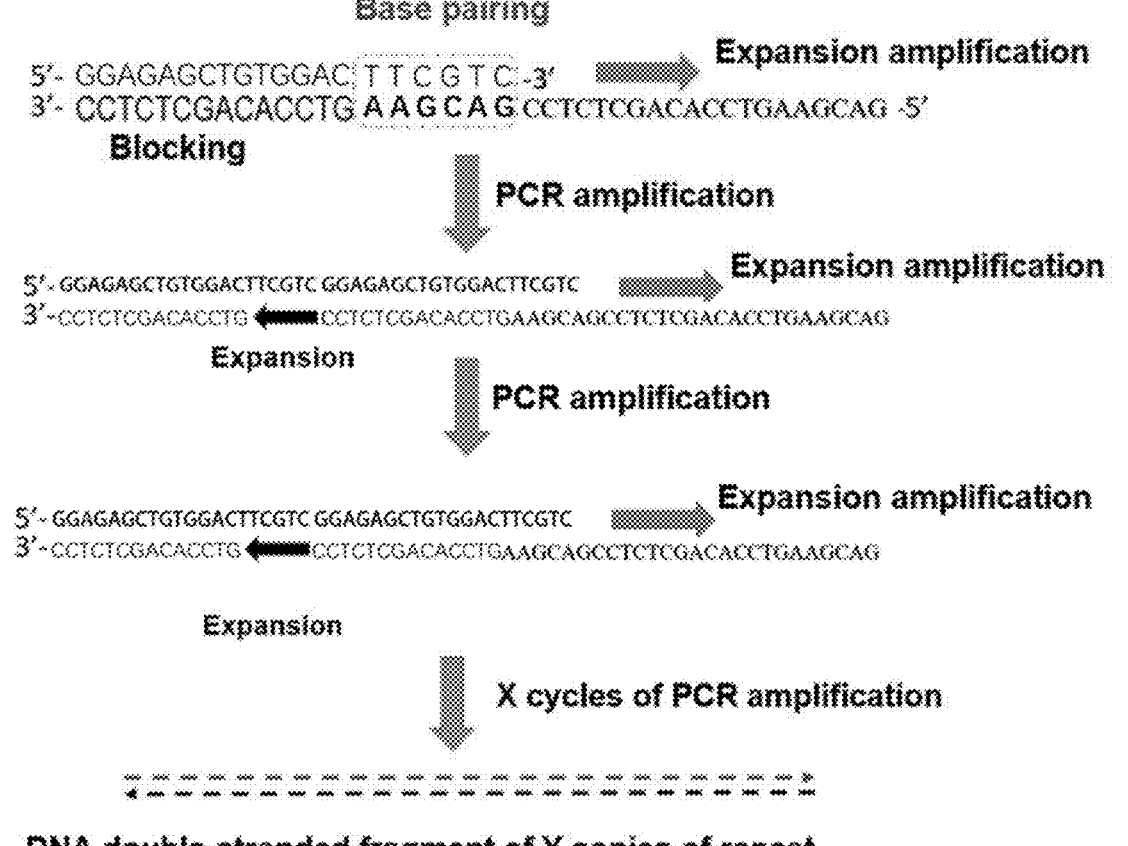
FIG. 4 shows a specific embodiment of BPRE according to some embodiments, using the following sequences: RU (repeat unit): 5'-GGAGAGCTGTGGACTTCGTC-3' (SEQ ID NO:1); TP (template primer or extension primer; the underlined part involves the paired bases of TP and RU): 5'-GACGAAGTCCACAGCTCTCCGACGAA-3' (SEQ ID NO:2); BP (blocking primer): 5'-GTCCACAGCTCTCC-3' (SEQ ID NO:3)

According to the base sequence composition of RU (repeat unit) (as shown in FIG. 4), TP (template primer, or extension primer) and BP (blocking primer) were designed respectively, and related sequences were synthesized in the form of single-stranded DNA primers (Beijing RuiBiotech Co., Ltd.). The maximum demand for primers as raw materials was 1 OD (about 33 micrograms of dry powders), and the minimum demand for primers as raw materials was 0.1 OD (about 3.3 micrograms of dry powders).

```
RU:
                                          (SEQ ID NO: 1)
5'-GGAGAGCTGTGGACTTCGTC-3'

TP:
                                          (SEQ ID NO: 2)
5'-GACGAAGTCCACAGCTCTCCGACGAA-3' (the underlined
part involves the paired bases of TP and RU)

BP:
                                          (SEQ ID NO: 3)
5'-GTCCACAGCTCTCC-3'
```

Example 2 Effect of the Molar Ratio of RU, TP, and BP in the PCR Reaction System on the Reaction The above dry powders of the primers were dissolved in distilled water to 100 μM, and the three primers (RU:TP:BP) were mixed based on different molar ratios to form mixed stock solutions, wherein the final concentration of RU in the mixed solution was 4 μM. Eppendorf PCR instrument was used as PCR instrument. Taq DNA polymerase (Taq, Vazyme, P515-02) was used in the PCR reaction. The stock solution with three primers was diluted by mixing with amplification enzyme solution, PEG4K (solarbio, P8240) solution, and NaCl solution, until the final concentration of RU primer was 400 nM. The amplification enzyme was at 1× working concentration, and the final reaction system range was 10-20 μL.

After the configuration of the amplification reaction system, a cyclic nested heating and cooling amplification was performed to synthesize repetitive double-stranded DNA molecular fragments. The heating conditions of the PCR cycle were as follows:

95° C. 2 minutes
95° C. 15 seconds
70° C. 15 seconds
72° C. 5 minutes

Due to the use of the short-term heating and cooling expansion for targeted amplification, the reaction time for preparation was generally within 1-2 hours.

Figure 5:
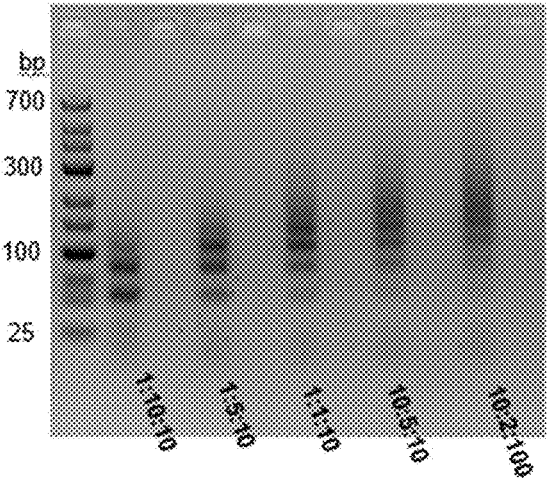
FIG. 5 shows the effect of the molar ratio of RU, TP and BP in the PCR reaction system on the reaction in the method of the invention (the ratio in the figure is the molar ratio of RU:TP:BP)

Different molar ratios (RU:TP:BP) had significant effects on the amplification efficiency and product band. As shown in FIG. 5, the optimal molar ratio for RU:TP:BP was 1:1:10, and such a ratio resulted in obvious product band (DNA marker; DSBIO; Low Ladder) and relatively high specificity. Thus, the molar ratio for RU:TP:BP used in the following experiments was 1:1:10.

Example 3 Effects of PEG Molecular Weight and Concentration in the PCR Reaction System on the Reaction In the PCR reaction system of the invention, PEG can be used as a synergist for the PCR reaction to improve the amplification efficiency.

Figure 6:
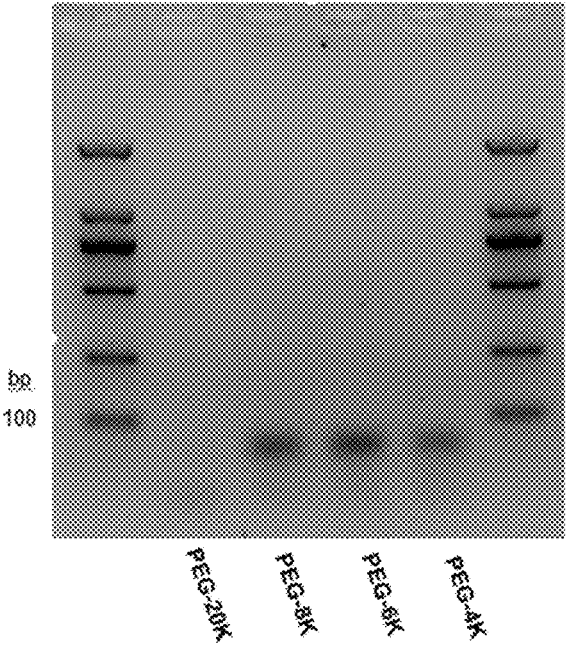
FIG. 6 shows the effect of PEG molecular weight (A) and PEG concentration (B) in the PCR reaction system on the reaction in the method of the invention.
Figure 6:
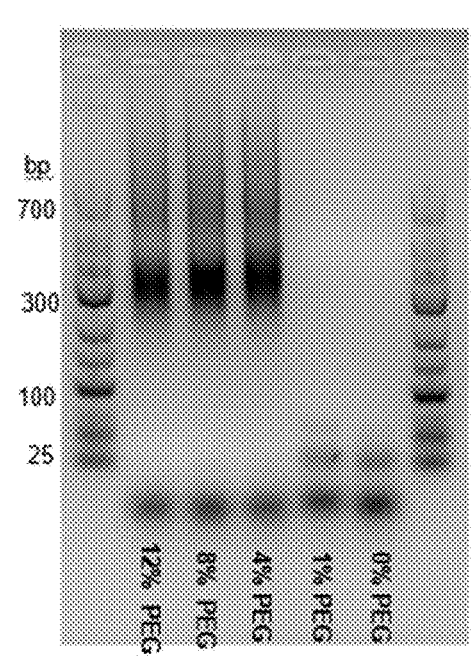

FIG. 6A showed the catalytic effects of the solutions of PEGs with different molecular weights (solarbio) at the same concentration (4 wt %) in the PCR reaction. As shown in the figure, PEG molecules with 4-8 k molecular weights can catalyze the pairing of the complementary bases (DNA marker; Tiangen; D2000), thereby promoting the incidence of amplification and extension reaction, while PEG molecules with molecular weights exceeding 20K can hardly result in amplification products.

On the other hand, FIG. 6B showed that when the PEG (PEG4K) concentration in the reaction system was lower than 4 wt % (DNA marker; DSBIO; Low Ladder), the entire extension reaction can hardly occur. Only when the PEG concentration reached a certain threshold, the entire reaction continued.

Figure 7:
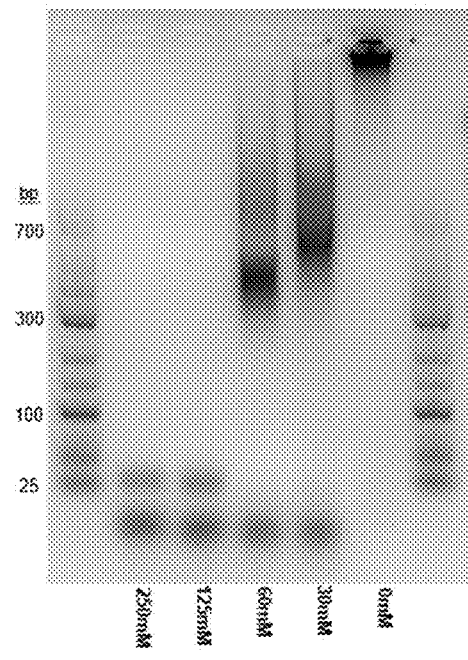
FIG. 7 shows the effect of NaCl solution concentration in the PCR reaction system on the reaction in the method of the invention.

Example 4 Effect of NaCl Solution Concentration in the PCR Reaction System on the Reaction Due to the presence of salt-sensitive molecular PEG4K in the reaction system, the amplification efficiency of DNA products can be regulated by different salt concentrations. There are batch differences in the salt solution residue for different batches of synthesized DNA primers. Thus, in order to ensure the consistency of amplification efficiency among batches and obtain the optimal amplification effect, the salt concentration sensitivity can be tested for different batches of single-stranded primers, so as to select the optimal salt ion concentration for this batch according to the experimental results. The NaCl solution was used as a calibration reagent, and in case of having 4 wt % of PEG4K at the same concentration, different concentrations of NaCl were used in the aforementioned experiment. As shown in FIG. 7, in this experimental system, when a 60 mM NaCl solution was added, the amplification band was more unitary than those under other conditions; when the concentration was higher than this concentration, the PCR amplification reaction was suppressed; and when the concentration was lower than this concentration, the tailing phenomenon was relatively significant in the amplification product and the product size was greatly distorted (DNA marker; DSBIO; LowLadder).

Example 5 Relationship Between the Length of Repetitive Double-Stranded DNA and the Number of Heating and Cooling Cycles This Example showed the relationship between the copy number of repeat units contained in the obtained PCR product and the number of heating and cooling cycles in the PCR reaction.

Figure 8:
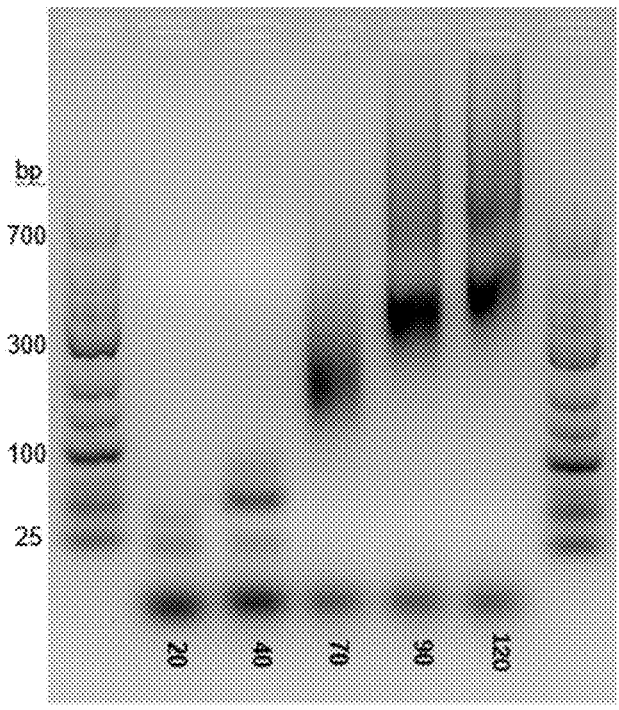
FIG. 8 shows the relationship between the double-stranded repetitive DNA product and the number of heating and cooling cycles in the method of the invention (the numbers 20, 40, 70, 90, and 120 in the figure represent the number of heating and cooling cycles in the PCR reaction)

As shown in FIG. 8, it was demonstrated that the number of cycles was positively correlated to the copy number of repeat units (repeats). When the number of amplification cycles was relatively lower, only 2-3 repetitive DNA double-stranded molecules were generated by amplification. When the number of amplification cycles was increased to 90 cycles, the repetitive double-stranded DNA molecule with more than 20 copies was generated, and the high-copy DNA repeat product was relatively unitary (DNA marker; DSBIO; Low Ladder).

The produced double-stranded repetitive DNA product can be connected to the commonly used carrier vector for sequencing detection and permanent storage. The amplification product can also be directly used in other experiments.

Example 6 Determination of the Copy Number of Repeat Units in the Repetitive Double-Stranded DNA The repetitive DNA sequence obtained in the above Example was connected to a PUC19 blue-white spot screening system (pUC19 plasmid provided in Tiangen DH5a competent cell). After sequencing detection (Beijing RuiBiotech Co., Ltd.), a DNA double-stranded molecule having 45 copies of repeat units without any base mutation was obtained. The whole production process took about 1 hour. The molecular weight of the produced DNA was shown in the gel electrophoresis. The cost of the reagents and materials for production was approximately RMB 30.

Figure 9:
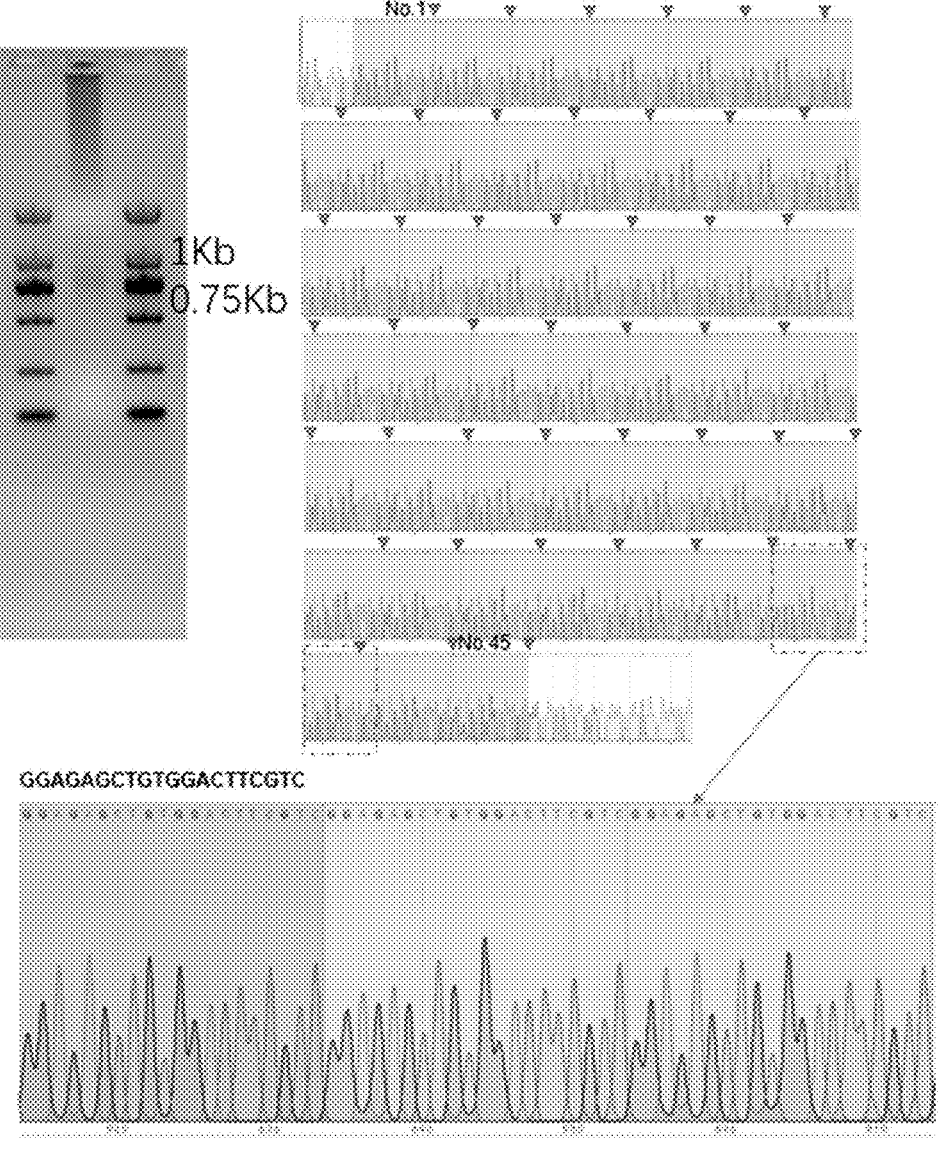
FIG. 9 shows the determination of the copy number of the repeat units included in the obtained PCR product (double-stranded repetitive DNA product) by gel electrophoresis method and sequencing method, wherein the sequence GGAGAGCTGTGGACTTCGTC (SEQ ID NO:1) is involved.

There were CAG.CTG repetitive structures inside the synthesized DNA double-strand with 45 copies of repeat units, and thus it was quite easy to form internal sliding structures in the single-strand and the difficulty of synthesis was greatly increased. The existing DNA synthesis methods (such as Gene SOE) can greatly increase the synthesis period or the error rate of DNA bases. As shown in FIG. 9, after the verification by electrophoresis and sequencing (Beijing RuiBiotech Co., Ltd.), this problem can be avoided to the greatest extent through synthesizing the DNA repeats by the way of synthesizing while blocking in the method of the invention, and thus medium- and high-copy DNA repeats without any base mutation or error were obtained.

Figure 10:
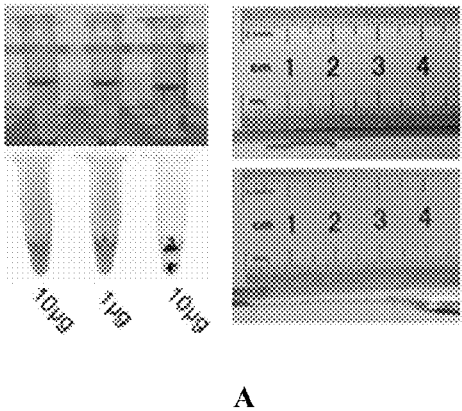
FIG. 10 shows that the PCR product (double-stranded repetitive DNA product) obtained by the method of the invention can be used as a template, and after further PCR amplification and processing, a DNA affinity gel (A) is obtained, which can be used as a drug sustained-release material (B, sustained-release profile of doxorubicin).
Figure 10:
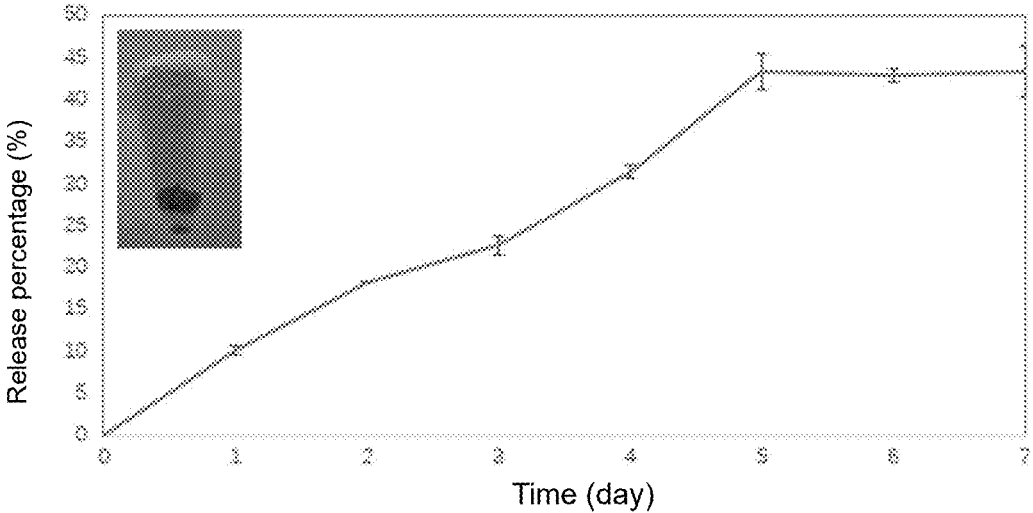

Example 7 Repetitive Double-Stranded DNA for the Formation of DNA Affinity Gel and the Drug Sustained-Release The repetitive double-stranded DNA produced in Example 6 was used as the template, and RU and TP were used as primers, for carrying out the ordinary PCR amplification. The amplification product was purified and subjected to heat shock at 85° C. After cooling, the crosslinking occurred among DNA molecules to form the DNA affinity gel (as shown in FIG. 10A, the left bottom was an imaging picture of the DNA gel under the DNA dye gelsafe (Yuanpinghao Bio)). The generated DNA gel possessed a good ductility, and had a good sustained-release function for DNA affinity molecule (such as doxorubicin). FIG. 10B showed the 7-day sustained-release profile of doxorubicin (Yuanye Bio-Technology; S17092-25 mg). The experimental method was as follows: a doxorubicin solution (0.125 μg) was added during the DNA gel production, the produced gel was incubated at 37° C. in ultrapure water, and the specific absorption peak of doxorubicin was detected at 490 nm in the solution every 24 hours by the microplate reader (SpectraMax M5). The experimental results showed that the DNA gel can maintain the drug sustained-release effect for five days, and had a good drug sustained-release function.

In general, the synthesis of moderately and highly repetitive sequences by the blocking RCR method of the invention is a synthesis method in which new copies are added while the synthesized repeats are blocked. This method possesses the characteristics such as low synthesis cost, simple operations and short time consumption, with no need for complicated instruments. The entire reaction system is completely based on the traditional DNA chain amplification system. The reaction process only requires a single biologically active molecule, thereby reducing the cost. Moreover, the entire process is performed in a distributed and sectional manner, and the length and copy number of the product can be controlled by the number of reaction cycles. Thus, the present method has significant advantages over the existing synthesis methods.

INDUSTRIAL PRACTICALITY

The copy number of repetitive DNA molecules is directly related to many biological functions and the molecular materials, such as chromosome structure regulation, cell cancerization, species evolution, DNA affinity gel, and DNA self-assembly nanostructure. The simple and efficient production of repeats of arbitrary DNA sequences and repeats with arbitrary copies will have important values in biology and material science, and will meet vast market demands.

Those skilled in the art should understand that, although the invention is described in details with reference to the above Examples, the invention is not limited to these specific Examples. Based on the methods and technical solutions taught by the invention, those skilled in the art can make appropriate modifications or improvements without departing from the spirit of the invention, and the equivalent embodiments thus obtained are all within the scope of the invention.

---

What is claimed is:

1. A kit for synthesizing a DNA sequence comprising repeat units, the kit comprising a PCR reaction system, wherein the PCR reaction system comprises a single repeat unit of the repeat units, an extension primer and a blocking primer, wherein the extension primer consists of: from its 3' end to its 5' end, a sequence consisting of n nucleotides, the blocking primer, and the sequence consisting of n nucleotides, wherein n is an integer between 3 and 20;

the single repeat unit of the repeat units consists of: from its 5' end to its 3' end, a nucleotide sequence fully complementary to the blocking primer and a nucleotide sequence fully complementary to the sequence consisting of n nucleotides wherein, when the 3' end of the extension primer is connected in tandem to the 5' end of the blocking primer, a connected product formed by the extension primer and the blocking primer consists of a sequence fully complementary to two of the repeat units;

wherein the PCR reaction system further comprises polyethylene glycol (PEG), the PEG has a molecular weight between 2,000 Da and 20,000 Da, and the PEG has a concentration from 4 wt % to 20 wt % in the PCR reaction system; and wherein the PCR reaction system further comprises NaCl, with a concentration from 20 mM to 60 mM.

2. The kit according to claim 1, wherein:

a) the molar ratio of the single repeat unit, the extension primer, and the blocking primer in the PCR reaction system is 1:1-10:1-40; and/or b) the PCR reaction system further comprises a Taq DNA polymerase.

3. The kit according to claim 2, wherein the molar ratio of the single repeat unit, the extension primer, and the blocking primer in the PCR reaction system is 1:1:10.

4. The kit according to claim 1, wherein the DNA sequence contains low copies of the repeat units or moderate copies of the repeat units or high copies of the repeat units.

5. The kit according to claim 4, wherein the DNA sequence contains moderate copies of the repeat units or high copies of the repeat units.

6. The kit according to claim 1, wherein the NaCl has a concentration from 30 mM to 60 mM.

7. The kit according to claim 1, wherein the integer between 3 and 20 is an integer from 4 to 10.

8. The kit according to claim 1, wherein the PEG has a molecular weight of 4,000 Da, 6,000 Da, or 8,000 Da.

9. The kit according to claim 1, wherein the PEG has a concentration of 4 wt %, 8 wt %, or 12 wt %.

* * * * *